United States Patent [19]
Liang et al.

[11] Patent Number: 5,648,003
[45] Date of Patent: Jul. 15, 1997

[54] SURGICAL GLOVE THAT PROTECTS AGAINST INFECTION BY PROVIDING HEAT IN RESPONSE TO PENETRATION THEREOF BY A MEDICAL INSTRUMENT AND METHOD THEREFOR

[76] Inventors: David H. Liang, 970 Altschul Dr., Menlo Park, Calif. 94025; Hank C. K. Wuh, 33 Third St., Los Altos, Calif. 94022

[21] Appl. No.: 432,216

[22] Filed: May 1, 1995

[51] Int. Cl.⁶ .................................................. H05B 3/36
[52] U.S. Cl. ...................... 219/211; 219/528; 219/544; 219/549; 2/161.7
[58] Field of Search .................... 219/211, 544, 219/528–529, 548–549; 604/292; 2/161.7, 167

[56] References Cited

U.S. PATENT DOCUMENTS

| | | | |
|---|---|---|---|
| 1,215,610 | 2/1917 | Bloomer | 219/549 |
| 3,781,514 | 12/1973 | Olson et al. | 219/211 |
| 4,021,640 | 5/1977 | Gross et al. | 219/211 |
| 4,201,218 | 5/1980 | Feldman et al. | 219/528 |
| 4,575,476 | 3/1986 | Podell et al. | 2/167 |
| 4,764,665 | 8/1988 | Orban et al. | 219/211 |
| 5,133,090 | 7/1992 | Modak et al. | 604/292 |
| 5,335,373 | 8/1994 | Dangman et al. | 604/292 |
| 5,357,636 | 10/1994 | Dresdner et al. | 2/167 |

FOREIGN PATENT DOCUMENTS

| | | | |
|---|---|---|---|
| 1255303 | 1/1961 | France | 219/211 |
| 1415836 | 11/1975 | United Kingdom | 219/211 |
| 20244 | 11/1992 | WIPO | 2/161.7 |

*Primary Examiner*—Teresa J. Walberg
*Assistant Examiner*—Raphael Valencia
*Attorney, Agent, or Firm*—Peter J. Dehlinger; LeeAnn Gorthey

[57] ABSTRACT

A protective device that provides protection against infection by accidental skin puncturing. The device includes a flexible expanse, at least a portion of which has a multi-layer construction that includes (i) inner and outer, flexible, electrically conductive layers, and (ii) a flexible insulative sheet separating said conductive layers. A voltage applied across the two layers is effective to heat the tip of a needle, scalpel, or the like, when such pierces the cover, to a temperature effective to destroy at least a portion of the infectious agent.

18 Claims, 5 Drawing Sheets

SURGICAL GLOVE THAT PROTECTS AGAINST INFECTION BY PROVIDING HEAT IN RESPONSE TO PENETRATION THEREOF BY A MEDICAL INSTRUMENT AND METHOD THEREFOR

FIELD OF THE INVENTION

The present invention relates to a glove or finger-cot device designed to provide protection against infection by accidental puncture wounds caused by a sharp instrument.

BACKGROUND OF THE INVENTION

Increasingly, health care workers are at risk of infection by blood-transmitted viral agents, particularly HIV and hepatitis-causing viruses. Virus infection can occur by contact with an infected body-fluid, where the person handling the sample has an area of broken skin, usually on the hands. Infection can also occur when a person receives an accidental puncture wound with a contaminated needle or other sharp instrument.

Because of the often severe consequences of accidental infection by an infectious agent such as a blood-borne vital agent, it is now standard practice for health care workers in medicine, dentistry, and blood banking to wear surgical latex gloves as a protective measure. Although such gloves are effective against certain types of blood transfer, they provide only limited protection to the wearer against accidental puncture by contaminated needles or other sharp instruments.

A variety of protective glove devices designed to prevent or reduce the risk of accidental blood transfer by puncturing have been proposed. One type of protective glove employs a flexible, puncture-resistant material, such as a polymer filament or metal-filament weave material, to resist penetration by sharp objects. Gloves having various puncture-resistant features are disclosed in U.S. Pat. Nos. 5,187,815, 4,942,626, 4,864,661, 4,742,578, 5,070,543, 4,951,689, 4,901,372, and 5,200,263.

The basic, but conflicting needs in a puncture-proof glove are high resistance to puncturing, requiring a strong physical barrier, and good touch sensitivity, requiring a thin and flexible barrier. To date, these conflicting needs have not been resolved satisfactorily.

In a variant of the puncture-proof glove, the glove is provided with puncture proof pads at selected finger positions on the glove. These pads may be placed at fixed positions on the glove, as disclosed in U.S. Pat. No. 4,864,661, or may float within a pair of flexible-expanse layers, as disclosed in U.S. Pat. No. 5,259,069.

Another type of protective glove construction provides chambers within the glove's interior for holding anti-microbial agents in solution form, as disclosed, for example, in U.S. Pat. No. 5,335,373. Puncturing the glove then releases the agent, which can then help sterilize the puncture site or inhibit microbial growth at the puncture site. A limitation with this approach is that the events leading to a puncture wound usually happen quite quickly, before solution agents can be dispensed effectively onto the puncturing instrument or into the wound site.

It would thus be useful to provide a glove- or finger-protective device that provides significant protection against infection by accidental puncture wounds with contaminated needles or the like, and which, at the same time, can be designed with a total thickness and flexibility that gives good touch sensitivity through the glove material.

SUMMARY OF THE INVENTION

In one aspect, the invention includes a protective device for a hand or finger. The device includes a flexible polymeric expanse designed to fit over a hand or finger, where at least a portion of the expanse has a multi-layer construction that includes (i) inner and outer, flexible, electrically conductive layers, and (ii) a flexible, preferably low-elasticity insulative sheet separating the conductive layers.

An electrical source operatively connected to the layers functions to produce a current between the conductive layers, with penetration of the outer layer and insulating sheet by the tip region of a sharp object, such as a needle, to heat the tip region to a temperature of at least about 60° C.

Flexible polymer layers forming the multi-layer construction preferably include a high-elasticity inner layer, and one or more low-elasticity outer layers.

In one general embodiment, each conductive layer is formed of a dispersion of conductive particles held in a polymer matrix. In another embodiment, each conductive layer is formed by a substantially two-dimensional network of overlapping conductive filaments or fabric weave.

In one general configuration, the expanse has regions corresponding to inner finger portions of a hand or finger, and the multi-layer construction is confined substantially to the finger portions.

The device may further include (i) an antimicrobial compound stored in the multi-layer construction, and (ii) a mechanism for releasing the compound from a puncture site in the construction, in response to heat generated in the region of the site.

In another general aspect, the invention includes a method of reducing the level of an infectious agent carried on the tip of a pointed instrument. The method includes puncturing with the tip of the instrument a flexible, puncturable expanse having a multi-layer construction that forms part of a body covering, e.g., a hand or finger covering, and that includes (i) a flexible, electrically conductive layer, and (ii) a flexible insulative sheet covering the conductive layer. In response to electrical contact between the tip and the conductive layer, there is applied a current through the tip which is effective to heat the tip to a temperature of at least 60° C.

The expanse may further include a second conductive layer separated from the first-mentioned layer by the insulative sheet. The current is applied by placing a voltage of at least 9 volts across the two conductive layers. The current may also be applied at a level which is effective to dull the tip of the pointed surgical instrument or needle.

In a more general aspect, the invention includes a flexible skin covering for use in providing a protective electrical response when the covering is punctured by an electrically conductive object, such as a needle or scalpel, having a pointed tip region. The covering includes a flexible, high-elasticity expanse adapted to be placed against the skin, a flexible, low-elasticity polymer sheet that is at least partially coplanar with the expanse, and a flexible conductive layer formed from a dispersion of conductive particles in a polymer matrix, or from a substantially two-dimensional network of overlapping conductive filaments, sandwiched between the expanse and polymer sheet. The protective response is produced by an electrical source in the covering, when the tip region of the instrument is brought into contact with the conductive layer.

These and other objects and features of the invention will become more fully apparent when the following detailed description of the invention is read in conjunction with the accompanying drawings:

DETAILED DESCRIPTION OF THE INVENTION

I. Definitions

Unless indicated otherwise, the terms below have the following meanings herein:

A "multi-layer construction" includes both a laminate construction, i.e., where the layers forming the laminate are bonded to one another, and a non-bonded multi-layer construction, i.e., where separate layers forming the construction are held in place by physical contact with one another.

A "low-elasticity polymer film material" is one which tends to deform irreversibly, then puncture, when force is applied slowly to the film by a sharp object. The tendency to puncture, rather than deform, increases as the thickness of the film is reduced, e.g., from 10 mils down to 0.5 mils. Exemplary polymers for forming low-elasticity polymer films include polyalkylene polymers, such as polyethylene and polypropylene, polyvinyl polymers, such as polyvinyl chloride and polyvinyl acetate, polystyrene, saran films, polyester, polyurethane, polymethyl methacrylate, and cellulose acetate.

A "high-elasticity polymer film material" is a rubber or rubber-like film material, which tends to stretch, rather than irreversibly deform or break, on slow application of force against the film by a sharp object. Exemplary high-elasticity or elastomeric films are formed of such polymers as latex rubber, polyisoprene, neoprene rubber, polybutadiene, and silicone rubber.

II. Protective Glove Device

Figure 1:
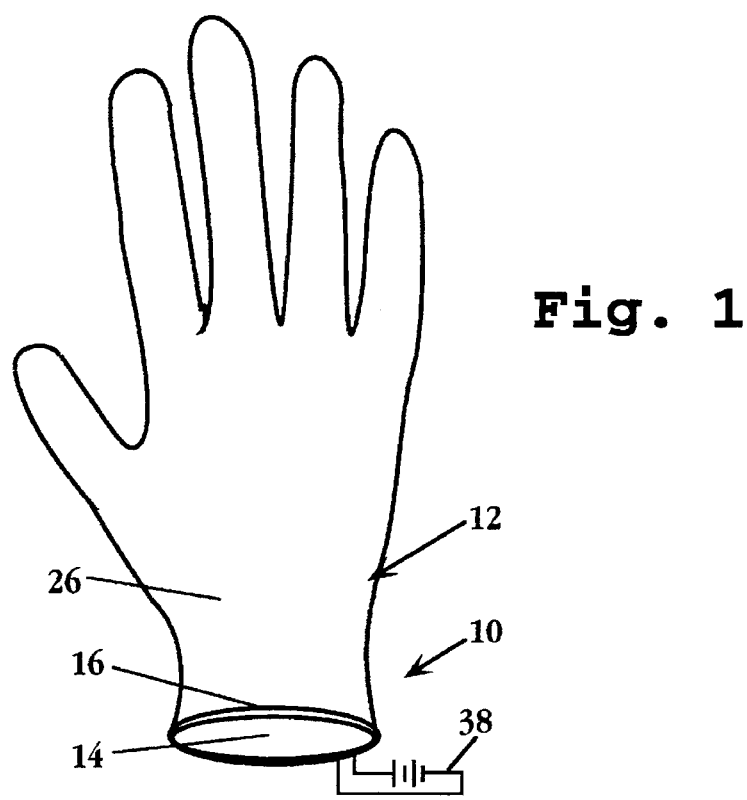
FIG. 1 shows a protective glove constructed in accordance with one embodiment of the invention.

FIG. 1 shows a protective surgical glove device 10 formed in accordance with the invention. The device includes a glove 12 formed of a flexible polymeric expanse 14 designed to fit snugly over a hand, where at least a portion of the expanse has the multi-layer construction 16 shown sectionally in FIG. 2. In the FIG. 1 embodiment, the multilayer construction encompasses the entire glove expanse. In the embodiment shown in FIG. 4, the multi-layer construction is confined to selected finger regions of a glove expanse.

Figure 2:
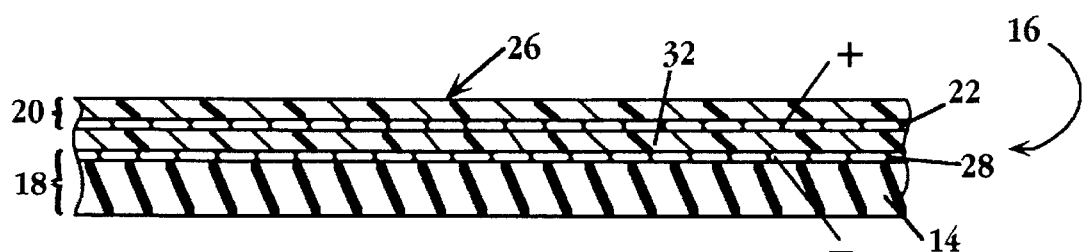
FIG. 2 is an enlarged cross-sectional view of the multi-layer construction in the glove.
Figure 3:
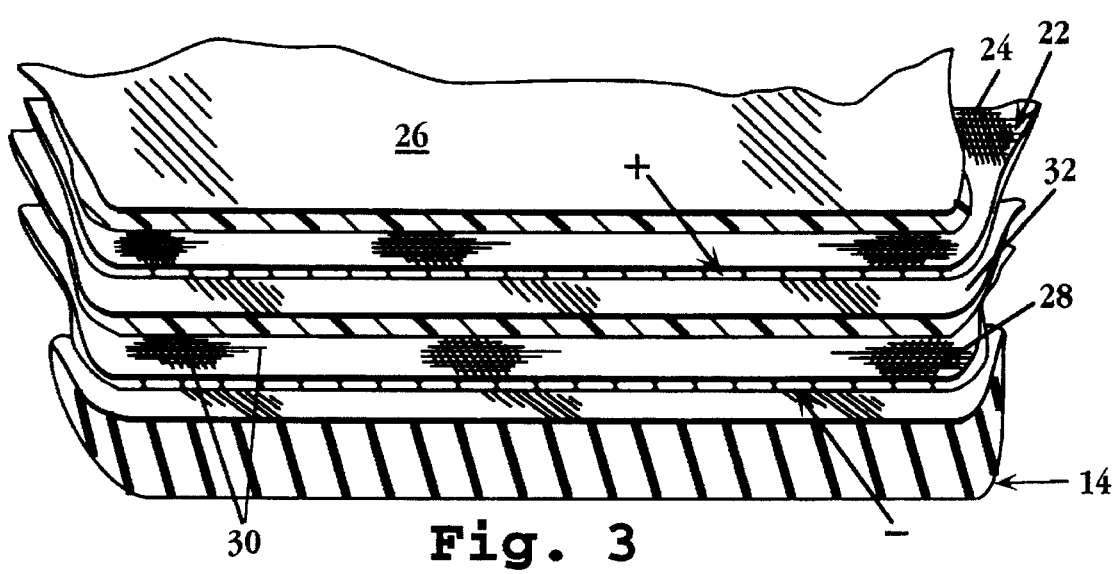
FIG. 3 illustrates the layers of the glove in the section represented in FIG. 2, but in exploded view.

With reference to FIGS. 2 and 3, the multi-layer construction in the glove includes inner and outer flexible, electrically conductive layers 18, 20, respectively. In the embodiment shown, outer layer 20 is formed of a substantially two-dimensional network 22 of overlapping conductive filaments, such as filaments 24 forming a fabric weave, as seen best in FIG. 3, and a flexible polymer covering sheet 26 which serves as an electrically insulative sheet for the conductive network. In the embodiment shown, the network and covering sheet are separate laminated layers in the construction. Alternatively, the network may be embedded in the covering layer, provided that the covering sheet insulates the network filaments on the glove's outer side.

Similarly, inner conductive layer 18 is formed of a substantially two-dimensional network 28 of overlapping conductive filaments, such as filaments 30 forming a fabric weave (FIG. 3), and a flexible polymer covering sheet which is provided by expanse 14, and which serves as an insulative sheet for the conductive network.

In another preferred embodiment, outer layer 20 and inner layer 18 are each by a dispersion of conductive particles in a polymer matrix film, as exemplified by "ELECTRODAG 504" (Acheson Colloids Company, Port Huron, Mich.).

With continued reference to FIGS. 2 and 3, the two conductive layers are separated by a flexible insulative sheet 32 which provides an electrical insulative barrier between the two conductive layer networks.

In a preferred embodiment, the innermost insulative sheet, i.e., expanse 14, is formed of a high-elasticity film material such as latex rubber or the like, as described in Section I. The expanse thickness is typically between about 2–30 mils, and preferably between 5–12 mils. Insulative sheet 32 and covering sheet 26, by contrast are preferably formed of relatively low-elasticity film material, as defined in Section I above, and typically are thinner than the lowermost expanse layer, having typical thicknesses between about 0.3–5, preferably about 0.5–3 mils. The purpose of the different sheet elasticities and thicknesses will be described below.

As indicated above, the conductive layers may be formed of a dispersion of conductive particles in a polymer matrix film. The network has a particulate density sufficient to ensure low resistance current flow throughout the network, i.e., such that current flow through the network is distributed over a large number of particles.

Alternatively, the two conductive layers may be formed as a weave of conductive filaments, such as manufactured by The Zippertubing Co. (Los Angeles, Calif.). The fabric is made by subjecting a thin fabric, such as polyester fabric, to an electroless plating process that chemically infuses the weave fibers with copper, silver or an alloy thereof, such as a copper/nickel alloy. The overall conductive properties of the fabric are determined by the density of weave and depth of plating. A preferred conductive fabric is one of the "Z-CLOTH" fabrics supplied by Zippertubing. These fabrics have a metal content between 14 and 27 weight percent.

The glove's multilayer construction can be made by conventional dipping or spraying techniques. For example, the inner latex sheet can be formed by one or more dips into latex suspension, until a desired thickness of, for example, 3–12 mils is achieved.

Following this, the latex expanse is dipped in the conductive dispersion coating repeatedly until the desired thickness is achieved. The conductive layer may also be formed by spraying of the latex expanse with the conductive dispersion. Alternatively, the expanse may be covered with sections of a filament weave material, such as described above, that will form the filament network of the inner conductive layer. The sections are preferably cut to provide substantially complete areal coverage, but glove flexibility between the edges of the fabric.

With the inner conductive layer so formed, the glove is then dipped into or sprayed with a suitable polymer solution to form the insulative sheet in the multi-layer construction. As noted in Section I, the polymer material is preferably a relatively non-elastic polymer, such as polyethylene, polypropylene, or polystyrene, and has a final thickness of preferably 3 mils or less.

After forming the insulative sheet, a second conductive layer is formed on the glove, as above, followed by a final coating to produce the covering layer in the outer conductive layer.

Completing the description of the glove device, and with reference again to FIG. 1, device 10 further includes an electrical source 38 operatively connected to the conductive layers of the glove for establishing a current between the two conductive layers when a pointed conductive metal object, such as a hypodermic needle, scalpel blade point, or the like, penetrates the outer conductive layer and insulative sheet and establishes electrical contact between the two conductive layers.

The electrical source may be a battery, as shown in FIG. 1, a charged capacitor, an alternating current electrical, or other source effective to produce the desired current levels in the device, when electrical contact is established between the two conductive layers in the glove. More generally, the current produced by the electrical source is sufficient to produce resistive heating at the tip region sufficient to heat the tip region of the instrument to a temperature effective to destroy infectious material present on the tip region, preferably 60° C. or higher. A preferred current source is a battery effective to place a voltage of at least 9 and preferably between 18–36 volts across the two conductive layers.

In the multilayer construction just described, the estimated instantaneous current measured with a 36 volt driving source is 3 amps, giving a calculated instantaneous power delivery of 118 watts. Thus, the electrical source in the device is preferably designed to generate a current of about 2–3 amps or greater, and an instantaneous power delivery of over 100 watts.

Figure 4:
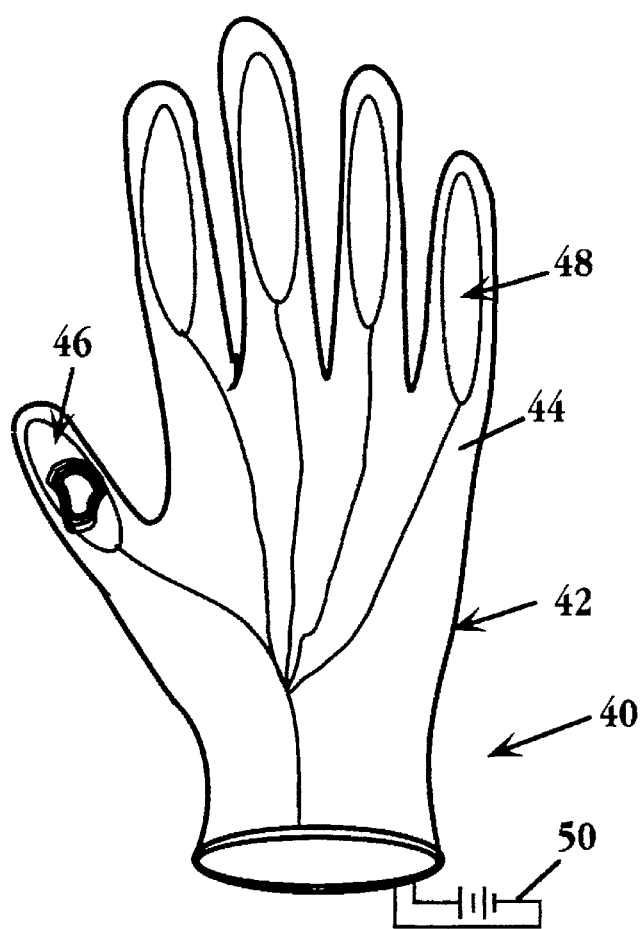
FIG. 4 illustrates an embodiment of a protective glove in which protective laminate regions are located in inner finger portions of the glove only.

FIG. 4 shows a glove device 40 constructed according to a second general embodiment of the invention. As above, the device includes a glove 42 formed of a flexible polymeric expanse 44 designed to fit over a user's hand. In this embodiment, the protective multilayer construction is composed of a series of pads, such as pads 46, 48, covering inner finger portions of the glove. Also shown are conductive connections between the five pads and one of the leads and an electrical source 50 in the device.

Figure 5:
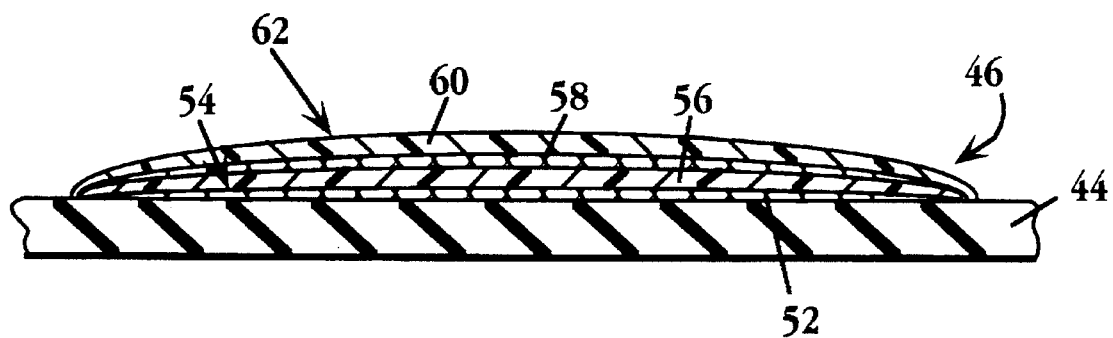
FIG. 5 is a cross-sectional view of a portion of the glove shown in FIG. 4.

The construction of pad 46, which is representative, is shown in enlarged sectional view in FIG. 5. The inner polymer layer in the pad is formed by a portion of expanse 44 which is composed of a high-elasticity film material similar to expanse 14 in the FIG. 1 embodiment. Formed over this portion of the expanse are (i) a filament network 52 which forms a lower conductive layer 54 in combination with the underlayer expanse, (ii) an insulative sheet 54 like sheet 32 in the FIG. 1 embodiment, (iii) a second filament network 58, and (iv) a covering sheet 60, like sheet 26 in the FIG. 1 embodiment, this sheet and underlying network 58 forming an upper conductive layer 62 in the pad. The two conducted layers are electrically connected to the electrical source, as illustrated in FIG. 4.

To form glove 40, finger regions of a latex glove are dipped or sprayed with successive conductive dispersion or conductive filaments and polymer layers, as described above for the FIG. 1 embodiment, until the multilayer construction making up each pad is complete. Each network is prepared with a connecting lead for attachment to one of the electrical source leads.

Alternatively, a planar multilayer construction lacking the lower expanse is prepared by successive layering, as above, to form a planar laminate from which pads are cut. The pads are then attached to the finger regions of a planar expanse by suitable bonding.

The embodiment of the glove device just described has the advantage of greater overall flexibility, since the less elastomeric portions of the device are confined to relatively small finger regions of the glove.

In a hybrid type of glove device, not shown, the glove's expanse is substantially completely covered, at least in those hand regions that are most at risk, by a series of adjoining plates or pads, each formed substantially as in the embodiment shown in FIG. 4.

This allows the glove to stretch easily to adapt to the wearer's hand, providing greater hand mobility, and at the same time, affording substantially complete-area protection against accidental puncturing.

Figure 6A:
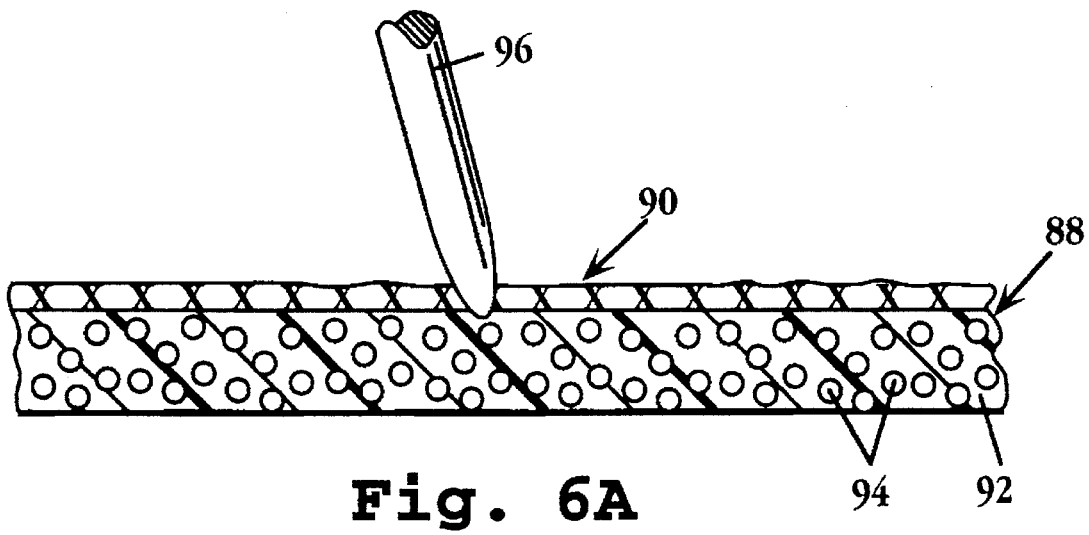
FIGS. 6A and 6B show steps in the activation of drug release in one embodiment of the invention.
Figure 6B:
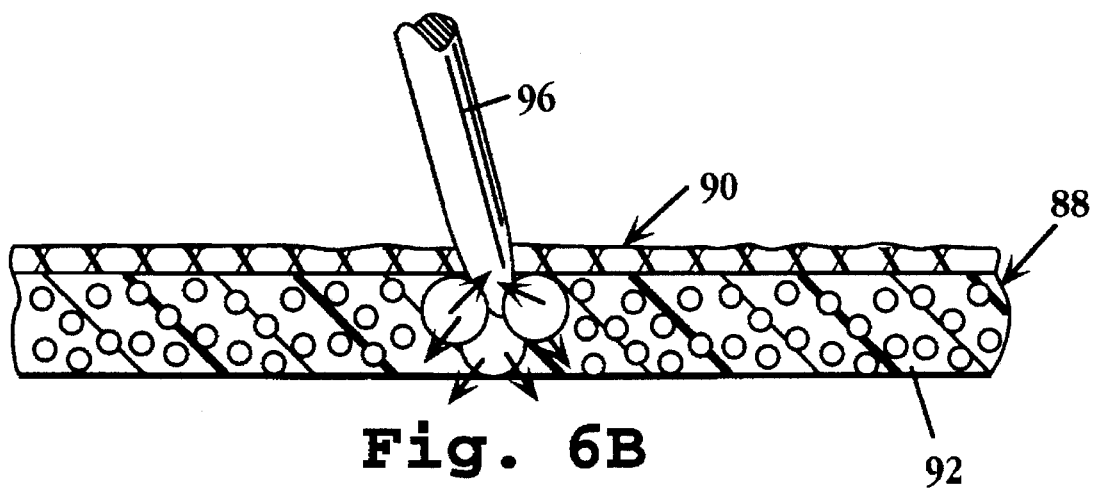

FIGS. 6A and 6B show, in fragmentary sectional view, another embodiment of the invention. The figures show the inner conductive layer 88 of a multi-layer construction 90 of the type detailed above. Embedded in the covering sheet are hydrogel microparticles, such as microparticles 94, which contain entrapped antimicrobial compound. The particles are designed for reversible phase transition between condensed and decondensed states, as the temperature of the particles is raised beyond a critical phase temperature, according to known particle construction.

The microparticles are loaded conventionally with antimicrobial compound in a decondensed phase (at elevated temperature), then condensed. The condensed particles are incorporated into and/or between layers in the multiwell construction, as indicated.

FIG. 6A shows the tip of a needle 96 as it first makes contact with the filament network in the lower conductive layer of the construction. At this stage, the compound-containing particles are in condensed (minimal volume) state, with the compound entrapped in the particles. With penetration of the lower covering sheet, and generation of $I^2R$ heat in the needle (FIG. 6B), the particles adjacent the needle are decondensed to an enlarged, porous state which allows release of the compound into the puncture region, as indicated. The microparticles are also referred to herein as compound-releasing means.

III. Protection Methods

The operation of the glove device in protecting a user against risk of accidental needle-stick infection, will be described with reference to FIGS. 7A and 7B, whose reference numbers correspond to those in FIG. 4.

Figure 7A:
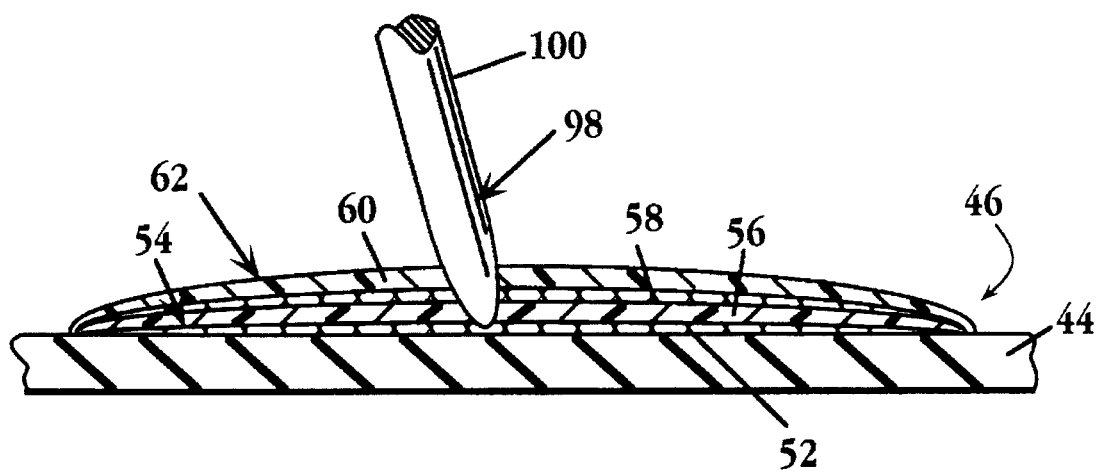
FIGS. 7A and 7B show progressive penetration of a needle tip region into and through the multi-layer construction of the invention.

FIG. 7A shows the initial puncturing event, when the tip region 98 of a needle 100 punctures the two low-elasticity sheets covering the more elastic expanse layer. The purpose of the thinner, less flexible sheets 56, 60 in the multilayer construction is to ensure puncturing of the sheets and activation of the heat-sterilizing feature of the invention when the needle first begins to penetrate through the multilayer construction (FIG. 7A), i.e., before it begins to deform and penetrate the lowermost, more flexible layer in the construction.

Figure 7B:
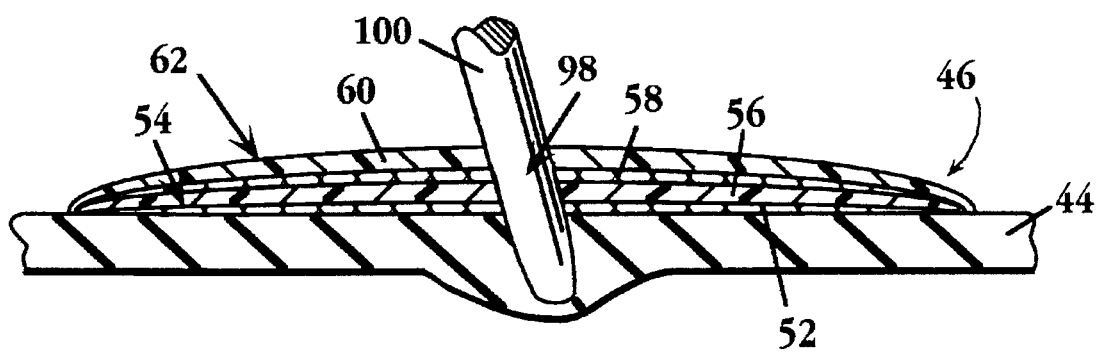

The thicker, more flexible lowermost layer serves as a barrier against puncturing, allowing more penetration and deformation before the layer is actually breached (FIG. 7B). As seen here, the needle is allowed to travel some distance through the multilayer construction, by virtue of its deformation of the lower elastic layer, before it actually breaks through the lower surface of the expanse. During this additional travel time, the needle continues to be heated and sterilized.

The multilayer construction described above was tested for its ability to reduce infectivity of HIV (human immunodeficiency virus) in human MT2 cells in culture. The study was performed by dipping a suture needle in media with live HIV, then passing the needle through the glove material into test wells containing human macrophage cells in culture. The results were tested at 0 and 18 volts applied to the material.

For each voltage level tested, up to 44 wells were inoculated. The wells were then incubated for two weeks under conditions favoring HIV replication in the cells, and assayed for the presence of HIV replication. With conventional latex gloves, about 70% of the inoculated wells contained replicating HIV. This percentage was reduced to about 19% when the contaminated needle was passed through the multilayer material of the invention, at 0 voltage potential across the conductive layers, indicating that the additional layers alone are effective in removing some virus from the needle. With application of an 18 volt potential across the conductive layers, only 9% of the wells (4 out or 44 tested) showed HIV infection.

At higher voltages tested (36–60 volts), the cells themselves were killed, so an assessment of HIV infection could not be made. Voltages higher than 18 are preferred, however, since higher voltage will create higher temperature and greater inactivation of the infectious agent.

The study shows that the heating events that occur on needle penetration are effective to at least partially sterilized a needle, in this case, an HIV-contaminated needle. The study illustrates the method, in accordance with one aspect of the invention, for reducing the level of an infectious agent carried on the tip of a pointed instrument.

The method involves the steps of puncturing with the tip of a sharp instrument a flexible, puncturable expanse having a multi-layer construction that forms part of a hand or finger covering and that includes (i) a flexible, electrically conductive layer, and (ii) a flexible insulative sheet covering said conductive layer. In response to electrical contact between the tip and the conductive layer, there is then applied a current through the tip effective to heat the tip to a temperature of at least 60° C.

In a preferred method, the multi-layer construction includes a second conductive layer separated from the first-mentioned layer by the insulative sheet, and the current is produced by applying across the two conductive layers, a voltage of preferably between 18–36 volts.

Figure 8A:
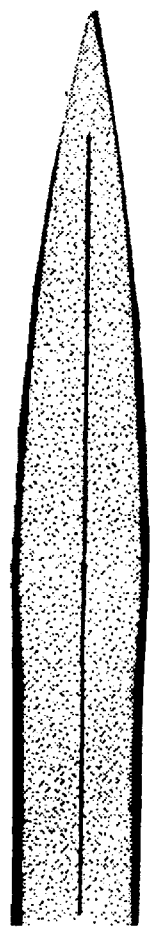
FIGS. 8A and 8B are photographs of a needle tip before and after heat treatment in accordance with one aspect of the invention.
Figure 8B:

Related studies conducted in support of the invention demonstrate that the heating induced by needle penetration is also effective to dull the needle tip slightly, as illustrated in FIGS. 8A and 8B. The figures show photographs of the pointed tip region 110 of a suturing needle before (FIG. 8A) and after (FIG. 8B) contact with the multi-layer construction of the invention, i.e., when the tip region is used to puncture the construction, and a voltage of 20 volts is applied across the two conductive layers in the construction. The needle was exposed to the current for a period of less than one second. As can be appreciated, the dulling effect on the needle tip also act to reduce the risk of infection by skin puncturing.

In a more general aspect, the invention provides a flexible skin covering for use in providing a protective electrical response when the covering is punctured by an electrically conductive object, such as a needle or scalpel, having a pointed tip region. The covering includes a flexible, high-elasticity expanse adapted to be place against the skin, a flexible, low-elasticity insulative polymer sheet that is at least partially co-planar with the expanse, and a substantially two-dimensional network of overlapping conductive filaments sandwiched between the expanse and the sheet. Also provided is electrical or current means for producing the protective response when such tip region is brought into contact with the network.

The protective response may be a current sufficient to heat-sterilize and/or dull the penetrating tip, an alarm, and/or release of an antimicrobial compound from the covering.

As an example, in the glove embodiment shown in FIG. 1, the covering expanse is formed by the glove's expanse 14, the network, by network 34, and the insulative low-elasticity sheet, by polymer sheet 34. The electrical means, which includes battery 36 and the outer conductive layer, is effective to produce a high-amperage current flow through the penetrating part of the needle tip, to cause at least partial heat sterilization of the tip.

Although the invention has been described with reference to particular embodiments and methods, it will be appreciated that various changes and modification may be made without departing from the invention. As one example, other types of protective covering devices, such as a finger cot, may readily be substituted for the glove constructions illustrated.

It is claimed:

1. A protective device for a hand or finger for use in providing a protective electrical response when the device is punctured by an electrically conductive medical instrument, comprising
   a flexible polymeric expanse designed to fit over a hand or finger, at least a portion of said expanse having a multi-layer construction of a thickness and flexibility suitable for use in a surgical glove, said multi-layer construction including
   (i) inner and outer, flexible, electrically conductive layers,
   (ii) a flexible polymer insulative sheet separating said conductive layers, and
   (iii) electrical means operatively connected to said layers for establishing a current between said layers, such that penetration of the outer layer and insulative sheet with said electrically conductive medical instrument is effective to heat a tip region of the instrument to a temperature effective to destroy at least a portion of infectious material present on the tip region.

2. The device of claim 1, wherein said conductive layers each are formed from a dispersion of conductive particles within a flexible polymer matrix.

3. The device of claim 1, wherein said conductive layers each are formed from a two-dimensional network of overlapping conductive filaments.

4. The device of claim 1, wherein said conductive layers each include a flexible polymer covering sheet, and the flexible polymer covering sheet in the inner layer is formed of a high-elasticity polymer film material, and the flexible polymer covering sheet in said outer layer and the insulative sheet are both formed of a low-elasticity polymer film material.

5. The device of claim 1, wherein said expanse has regions corresponding to inner finger portions of a hand or finger, and said multi-layer construction is confined substantially to said finger portions.

6. The device of claim 1, wherein said electrical means includes a battery effective to establish a voltage of between 9–45 volts between said layers.

7. The device of claim 1, wherein said temperature is at least 60° C.

8. The device of claim 1, which further includes (i) an anti-microbial compound stored in said multilayer construction, and (ii) means for releasing said compound from a puncture site in said construction, in response to heat generated in the region of said site.

9. The device of claim 7, wherein said releasing means includes a hydrogel polymer which contains said compound in a condensed polymer phase, and which is effective to release said compound when the polymer undergoes heat-activated decondensation.

10. A method of reducing the level of an infectious agent carried on a tip of a pointed instrument, comprising puncturing with the tip of the instrument a flexible, puncturable expanse having a multi-layer construction that forms part of a hand or finger covering and that includes
(a) a flexible, electrically conductive layer, and
(b) a flexible insulative sheet covering said conductive layer; and applying a current through said tip, in response to electrical contact between the tip and the conductive layer, that is effective to heat the tip to a temperature effective to destroy at least a portion of infectious material present on the tip.

11. The method of claim 10, wherein said expanse further includes a second conductive layer separated from the electrically conductive layer of (a) by said insulative sheet, and said applying includes applying a voltage of at least 9 volts across the two conductive layers.

12. The method of claim 11, wherein the voltage applied across said layers is between 9 and 45 volts.

13. The method of claim 10, wherein said infectious agent is human immunodeficiency virus.

14. The method of claim 10, wherein said current is applied at a level which is effective to dull the tip of the pointed instrument, when current is applied through it.

15. The method of claim 10, wherein said temperature is at least 60° C.

16. A flexible skin covering for use in providing a protective electrical response when the covering is punctured by an electrically conductive object, such as a needle or scalpel, having a pointed tip region, said covering comprising a flexible, high-elasticity expanse adapted to be placed against the skin, a flexible, low-elasticity polymer sheet that is at least partially co-planar with said expanse, a flexible conductive layer disposed between said expanse and sheet, and electrical means for producing such protective response when such tip region is brought into contact with said conductive layer.

17. The covering of claim 16, wherein said polymer sheet has a thickness between 0.5 and 3 mils.

18. The covering of claim 16, wherein said protective response is current flow between such tip region and the conductive, at a current level effective to heat the tip to a temperature effective to destroy infectious material present on the region.

* * * * *